United States Patent [19]

Bressi et al.

[11] Patent Number: 5,801,191

[45] Date of Patent: Sep. 1, 1998

[54] TAXOIDS

[75] Inventors: Jerome C. Bressi; James G. Douglass, III, both of San Diego; Allen Seligson, Poway; Milos Sovak, LaJolla, all of Calif.

[73] Assignee: Biophysica Foundation, LaJolla, Calif.

[21] Appl. No.: 457,674

[22] Filed: Jun. 1, 1995

[51] Int. Cl.$^6$ .................... A61K 31/335; C07D 305/14
[52] U.S. Cl. .................... 514/449; 549/448; 549/510; 549/511
[58] Field of Search .................... 514/449; 549/510, 549/511, 448

[56] References Cited

U.S. PATENT DOCUMENTS

| | | | |
|---|---|---|---|
| 4,942,184 | 7/1990 | Haugwitz et al. | 514/449 |
| 5,278,324 | 1/1994 | Kingston et al. | 549/510 |
| 5,362,831 | 11/1994 | Mongelli et al. | 526/304 |

FOREIGN PATENT DOCUMENTS

| | | | |
|---|---|---|---|
| 0 537 905 A1 | 4/1993 | European Pat. Off. | |
| WO 93/24476 | 12/1993 | WIPO | |

OTHER PUBLICATIONS

Ueda et al., "Synthesis and Antitumor Evaluation of 2'-Oxycarbonylpaclitaxels (Paclitaxel-2'-Carbonates)", Biorg. & Med. Chem. Lett. (1994), 4:pp. 1861-1864.

Vyas et al, "Phosphatase-Activated Prodrugs of Paclitaxel", Amer. Chem. Soc. (1995), pp. 124-137.

Greenwald et al., "Highly Water Soluble Taxol Derivatives: 7-Polyethylene Gycol Carbamates and Carbonates", J. Org. Chem. (1995), 60:pp. 331-336.

Chen et al., "Taxol® Structure-Activity Relationships: Synthesis and Biological Evaluation of Taxol Analogs Modified At C-7", Biorg. & Med. Chem. Lett (1994), 4:pp. 2223-2228.

Nicolaou et al., "Design, synthesis and biological activity of protaxols", Nature (1993), 364:pp. 464-466.

Greenwald et al., "Highly WaterSoluble Taxol Derivative: 2'-Polyethleneglycol Esters As Potential Prodrugs", Bio. & Med. Chem. Lett. (1994), 4:pp. 2465-2470.

Ueda et al., "Novel Water Soluble Phosphate Prodrugs of Taxol® Possessing In Vivo Antitumor Activity §", Biorg. & Med. Chem. Lett. (1993), 3:pp. 1761-1766.

*Primary Examiner*—Ba K. Trinh
*Attorney, Agent, or Firm*—Richard F. Trecartin

[57] ABSTRACT

Novel taxoids are provided having enhanced water solubility and/or improved pharmacological properties as compared to paclitaxel. The subject taxoids comprise a functional group attached to a paclitaxel at the C-2' and/or C-7 position by a linking group. Functional groups present in the subject taxoids may be hydrophilic chains, groups capable of in vivo conversion to hydrophilic chains, targeting moieties capable of specifically binding with cellular receptors and water soluble polymers of at least 5 kD. The subject taxoids find use in the treatment of hosts suffering from a cellular proliferative disease.

23 Claims, 10 Drawing Sheets

ARROWS INDICATE DAYS OF INJECTION

TAXOIDS

TECHNICAL FIELD

The technical field of this invention is novel taxoids and their use in the treatment of cellular proliferative diseases.

BACKGROUND

Paclitaxel (TAXOL®) is a biologically active agent which is a member of the taxane family of diterpenes and was originally isolated from the bark of *Taxus brevifolia* L. Wani et al., J. Am. Chem. Soc. (1971) 93:2325. Paclitaxel promotes the assembly of microtubules from tubulin dimers and stabilizes microtubules by preventing their depolymerization. In addition to prevention of depolymerization, paclitaxel induces the formation of abnormal arrays of microtubules throughout the cell cycle, as well as the formation of multiple asters of microtubules during mitosis. This activity results in the inhibition of normal cell division.

Because of its effect on normal cell division, paclitaxel possesses potent antineoplastic activity. The clinical efficacy of paclitaxel against several tumor systems has been demonstrated and paclitaxel is approved for clinical use in the treatment of ovarian and breast cancers.

Despite paclitaxel's promise as an antineoplastic agent, it has a number of drawbacks. For example, it is extremely insoluble in water and cannot therefore be formulated into physiologically acceptable compositions which are tolerated well by the host or patient. Paclitaxel's extreme insolubility in standard aqueous media (saline, dextrose etc.) requires formulation in emulsifying vehicles which induce side effects and limit its method of administration. Paclitaxel is currently administered in formulations comprising CremaphorEL® (polyethoxylated castor oil). However, this formulation requires additional medication to suppress the hypersensitivity to CremaphorEL® formulations. In many patients because of uncontrollable hypersensitivity TAXOL® (paclitaxel and CremaphorEL® formulation) is contraindicated. See Physician's Desk Reference (1994) 670.

The emulsions are also dose-limiting. Also, paclitaxel is known to partially precipitate, and the clinical practice requires an interposed filter in the i.v. line. This makes the doses delivered uncertain.

The pharmacologic properties of paclitaxel, as well as formulations of paclitaxel in emulsifying vehicles, are also not entirely satisfactory. Side effects include hypersensitivity, myelosuppression, neuropathy, alopecia, and cardio-toxicity, which occur in about 30% of patients. In addition, patients receiving paclitaxel often develop drug and multiple drug resistance.

The pharmacokinetics of paclitaxel have been studied with the following results. The plasma concentration of paclitaxel rapidly declines following infusion due to both distribution of the drug to the peripheral compartment and significant drug elimination. The mean steady state volume of distribution has been found to range from 42 to 162 $L/m^2$, indicating extensive extravascular distribution and/or tissue binding of paclitaxel. See Physician's Desk Reference (1994) 670. In some instances, it would be desirable for the paclitaxel agent to have different pharmacological properties, such as a longer half-life or a more specific tissue distribution profile.

In an effort to overcome the above problems associated with the low water solubility of paclitaxel, efforts have been made to produce paclitaxel derivatives (taxoids) which exhibit at least comparable cytotoxic activity to paclitaxel while also having improved water solubility and/or pharmacologic properties, particularly as prodrugs. See, for example, Uedq et al., Bioorganic & Medicinal Chemistry Letters (1993) 3:1761–1766; Nicolaou et al., Nature (1993) 364:464–466; Ueda et al., Bioorganic & Medicinal Chemistry Letters (1994) 4:1861–1864; Greenwald et al., Bioorganic & Medicinal Chemistry Letters (1994) 4:2465–2470; Chen et al., Bioorganic & Medicinal Chemistry Letters (1994) 4:2223–2228; Greenewald et al., J. Org. Chem. (1995) 60:331–336. Paclitaxel has been chemically modified via substitution reactions at the C-2' and C-7 positions. Paclitaxel derivatives substituted at these positions were reported in Magri & Kingston, J. Nat. Prods. (1988) 51:298–306.

While by adding hydrophilic groups one may improve the water solubility of paclitaxel, these groups must not seriously adversely affect the desired properties of paclitaxel. In order for paclitaxel to be active, it must be able to exert its physiological effect by appropriate binding, requiring its entry into the cell, the derivative must have a reasonable lifetime in the bloodstream of the host, bioavailability of the paclitaxel must be maintained at a cytotoxic level, and the derivative should not change the activity profile between normal and neoplastic cells adversely as compared to paclitaxel, among other factors.

It would also be desirable to enhance the activity profile between the target neoplastic cells and normal cells.

Therefore, there is continued interest in the development of new paclitaxel derivatives which differ from paclitaxel in both water solubility and pharmacological properties. Ideal paclitaxel derivatives would have cytotoxic activity comparable to, or greater than, paclitaxel while at the same time have improved water solubility and/or pharmacological properties.

Relevant Literature

Patents disclosing water soluble paclitaxel derivatives include 5,278,324 and 5,362,831. Published PCT application Ser. No. WO 93/24476 describes paclitaxel derivatives comprising paclitaxel covalently linked to polyethylene glycol (PEG).

Other references of interest include: Mathew et al., J. Med. Chem., 1992; 35(1):145–151; Deutsch et al., J. Med. Chem.,1989; 32(40:788–792; Veda Y, et al. Biorg. and Med. Chem. Lett., 1993; 3(8):1761–1766; Rimoldi et al., J. Natural Products, 1993; 56(8): 1313–1330; Chaudhary et al., J. Org. Chem., 1993; 58(15):3798–3799; Parness et al., Biochem. and Biophys. Res. Comm., 9182; 105(3): 1082–1089; Kingston et al., J. Nat. Prod., 1990; 53(1):1–12; Swindell et al., J. Med. Chem., 1991; 34(3):1176–1189; Kant et al., Biorg. Med. Chem. Lett., 1993; 3(11):pp. 2471–2474; Gueritte-Voegelein et al., J. Med. Chem., 1991; 34(3) :992–998; Zhao et al., J. Nat. Prod., 1991; 54(6):1607–1611; Chen et al., Biorg. Med. Chem. Lett., 1994; 4(18) :2223–2228; Greenwald et al., Biorg. Med. Chem. Lett., 1994; 4(20):2465–2470; Nicolaou et al. Agnew Chem. Int. Ed. Engl. 1994;33:1583–1587; Nicolaou et al. Nature, Jul. 29, 1993; 346:464–65; Vyas et al., Biorg. Med. Chem. Lett. 1993; 3(6):1357–1360; Vyas et al. ACS Publications 1995; 583:124–137.

SUMMARY OF THE INVENTION

Novel paclitaxel derivatives (taxoids) and methods of their use in the treatment of cellular proliferative diseases are provided. In the subject taxoids, functional groups are attached to paclitaxel at the C-2' and/or C-7 position via linking groups of varying chemical stability, and which in principle are cleavable, e.g. by hydrolysis or enzymatic mechanisms. Functional groups found in the subject taxoids include those groups which increase water solubility and/or provide for improved pharmacologic properties as compared to paclitaxel, e.g. groups which modulate the half-life of the active agent, and/or serve to target the active agent to a particular cell type. The subject taxoids which, being more water soluble than, and/or having pharmacologic properties superior to, paclitaxel, find use in the treatment of hosts, particularly human hosts, suffering from cellular proliferative diseases.

DESCRIPTION OF THE SPECIFIC EMBODIMENTS

Figure 1:
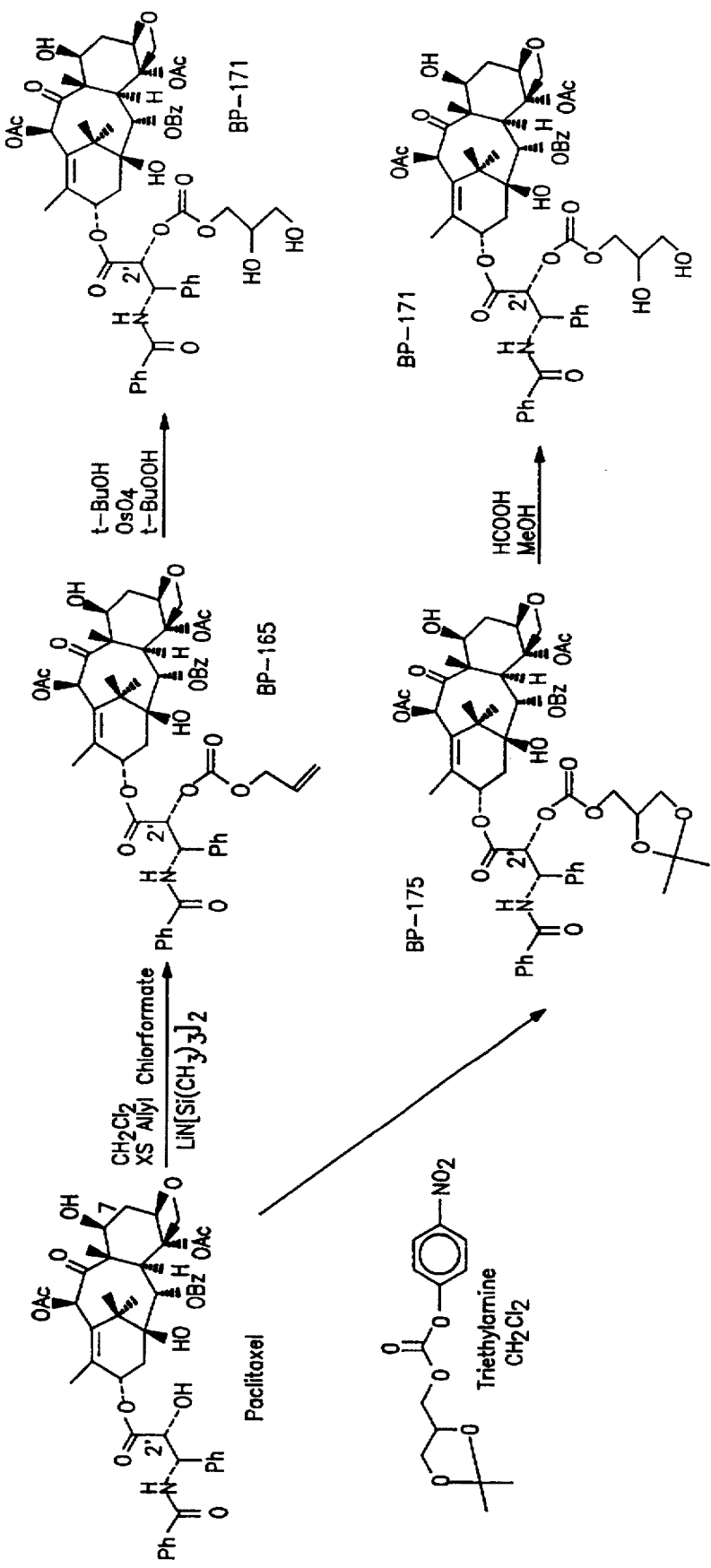
FIG. 1 provides the reaction scheme of two alternative routes for the synthesis of BP-171.

Novel paclitaxel derivatives (taxoids) having enhanced water solubility and/or improved pharmacologic properties as compared with paclitaxel are provided. The subject taxoids comprise conjugates of functional groups attached to paclitaxel at the C-2' and/or C-7 positions by linking groups, which may be hydrolytically cleavable or labile, particularly labile under physiological conditions, where the functional groups comprise hydrophilic groups, either small molecules or polymers, and/or targeting moieties. The subject taxoids find use in the treatment of hosts suffering from a wide variety of cellular proliferative diseases.

The paclitaxel may be the naturally occurring stereoisomer or an epimer, particularly at the C-7 position. Unless otherwise clear from the context, paclitaxel will intend both the naturally occurring stereoisomer and its epimers.

The monomeric compounds of the subject invention will have from one to two substituents of from 3 to 25 carbon atoms and from 2 to 12 heteroatoms, which may be nitrogen, chalcogen (oxygen and sulfur), phosphorus, boron and halogen (fluorine and chlorine). For the hydrophilic groups imparting water solubility, the substituents will be of from 3 to 12, usually 3 to 10 carbon atoms, having at least one heteroatom, usually nitrogen (amino) or oxygen (oxy), there being at least one heteroatom per 1.25 to 4 carbon atoms, preferably at least one heteroatom per 1.3 to 3 carbon atoms, exclusive of the functionality linking the carbon of the hydrophilic group to paclitaxel oxygen. Other heteroatoms which may be present include phosphorus and boron, particularly as their acid esters. The substituents may be aliphatic, aromatic, alicyclic, aliphatically saturated or unsaturated, or combinations thereof.

The targeting group will vary more widely depending on the target and the choice of compound for directing the conjugate to the target neoplasia.

The polymeric compounds will have at least one paclitaxel, usually at least one paclitaxel per 10kD, more usually at least one paclitaxel per 2kD, preferably about 1 paclitaxel in the range of about 200D to 1.5kD. The polymer will include an acidic group as a side chain.

The linking group will involve an ether or a non-oxo carbonyl group (C=O) and the nitrogen and sulfur analogs thereof, and may be a carboxyl group where the other valence of the carbonyl is bonded to carbon, oxygen, sulfur or nitrogen.

Taxoids of the subject invention may be described by the following formula:

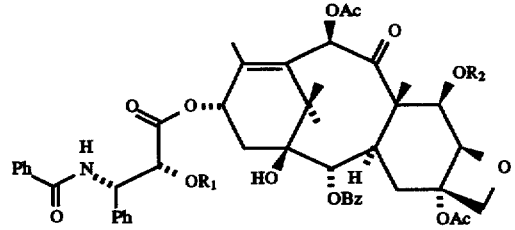

wherein $R_1$ and $R_2$ are one of OH, $R_5$, or $R_6$ with the proviso that at least one of $R_1$ and $R_2$ is other than OH and when $R_6$, there is only one $R_6$ and the paclitaxel is bonded to a unit of a polymer, which polymer is at least about 5kD.

$R_5$ represents a group comprising a functional moiety and a linking group which may be described by the formula:

wherein:

X is selected from O, S or NH, and Y is selected from O, S, NH or $CH_2$. Preferably, the selection of X and Y will be such that the linking group will have a physiological half-life under the conditions of use to achieve optimal pharmacological activity, frequently of not more than 24h, more frequently of not more than about 12h. Particular linking groups of interest include groups that are potentially cleavable by hydrolysis or enzymatic action, such as carbonate groups (where both X and Y are O, carbamate groups (where X is NH and Y is $CH_2$), urethane groups( where X is NH and Y is O), isourea (where X is NH and Y is NH), and the like.

n is an integer selected from 0–6, usually 0 to 4, and more usually 1–3 so as to provide for an aliphatic spacer chain which, if present, separates the functional group from the linking group.

m is an integer of 0 to 1, wherein m+n are in the range defined for n, when Y is $CH_2$.

Z is a monomeric or polymeric group, where the group may be hydrophilic and/or targeting to specific types of cells. When hydrophilic, Z will make the taxoid at least 10% more water soluble than paclitaxel, usually at least 100% more water soluble than paclitaxel, and preferably at least 500% more water soluble than paclitaxel, at 25° C.

When Z is monomeric and hydrophilic, Z is an organic group, which is aliphatic, alicyclic, aromatic, heterocyclic, or combinations thereof, aliphatically saturated or unsaturated, frequently free of any unsaturation, of from 2 to 12, usually 2 to 10, preferably 2 to 7 carbon atoms, which may be a straight chain or branched chain aliphatic group, having at least one heteroatom which is nitrogen or oxygen, preferably having at least 2 oxy groups, particularly hydroxy groups, wherein the number of heteroatoms will be at least one and up to one heteroatom per carbon atom, usually in the range of about 1 heteroatom per 1.25 to 4 carbon atoms; or heterocyclic of from 3 to 8, usually 3 to 7 carbon atoms and having 5 to 6 annular members, usually having from 1 to 3 annular heteroatoms, usually 1 to 2, preferably 2, particularly including oxygen, and a total of from 1 to 4, usually 1 to 3, preferably 2 to 3 heteroatoms, which include oxygen, nitrogen, phosphorus and boron; desirably the heterocycle is hydrolyzable under physiologic conditions, particularly being an acetal, ketal, orthoester, or cyclic ester, and nitrogen analogs thereof, comprising nitrogen, oxygen, phosphorus and boron heteroatoms, particularly oxygen. Of particular interest as substituents are polyhdroxyalkyloxy- carbonyl of from 3 to 6, usually 3 to 5 carbon atoms, having from 2 to 4 hydroxyl groups, particularly dihydroxypropoxy- and dihydroxybutoxy-carbonyl.

Specific taxoids comprising hydrophilic chain functionalities include 2'-(2",3"-dihydroxypropyl carbonoxy) paclitaxel, (BP-171); 2'-(2",3"-dihydroxypropyl carbamoxy) paclitaxel (BP-174); 2'-(1",2",6",7"-ol, heptane-4"-carbonoxy) paclitaxel (BP-189) and its C-7 epimer (BP-195); 2'(2",3",4"-trihydroxybutyl-carbonoxy)paclitaxel, (BP-191); 2'-($3^{11}$,4"-dihydroxybutyl-carbonoxy)paclitaxel, (BP-193); 2',7-di(2",3"-dihydroxypropyl carbonoxy) paclitaxel, (BP-177); 7-(2",3"-dihydroxypropyl carbonoxy) paclitaxel, (BP-179); 7-(2", 3"-dihydroxypropyl carbamoxy) paclitaxel (BP-187); 2'-(1",3",4"-trihydroxyisoureyl) paclitaxel; 7-(1",3"-diamino- 2"-carboxy)paclitaxel; 2'-(2", 4"-dihydroxythioureyl)paclitaxel; and the like.

Instead of comprising an aliphatic chain substituted with at least one hydrophilic group, Z may comprise a saturated heterocyclic group having at least one heteroannular member capable of hydrolysis in vivo into an hydroxyl or amino substituted aliphatic chain, and the like. Specific taxoids of interest include 2'-[(2-methylphospho-1,3-dioxolane-4-methoxy)carbonoxy] paclitaxel, 2'-[(5-methoxy-1,3-dioxolane-4-methoxy)carbonoxy] paclitaxel, 2'-[(4"-trihydroxybutylaminobenzoyl] paclitaxel, and the like.

Alternatively, Z may be a targeting moiety which serves to direct the taxoid to a specific cell or tissue type expressing a complementary member to which the targeting moiety specifically binds. The targeting moiety may be less than about 2.5kD, usually less than about 1 kD, and usually at least about 250D, more usually greater than about 500D. The targeting moiety may be a small organic molecule, which may be aliphatic, alicyclic, aromatic, heterocyclic, or combinations thereof, which has an affinity for a surface membrane receptor of a particular class of cells as a result of the receptor being specific for the class or upregulated when associated with neoplastic cells. Alternatively, the targeting moiety may be a protein, preferentially a monoclonal antibody directed against a tumor specific cell surface antigen, more particularly one which is not alternatively spliced to provide a soluble form. Of interest are targeting moieties which are specifically directed to tumor cells, or directed to specific organs with which the tumor is associated. These include organic molecules other than poly(amino acids) which have been shown to be specific for receptors associated with particular cell types, such as breast cells, ovarian cells, prostate cells, hematopoietic cells, muscle cells, etc.; specific classes of compounds include steroids, androgen receptor binding molecules, Anandron, Flutamide, Casodex, e.g. $N^3$- (3'-trifluoro-4'-cyanophenyl) 2,4-dioxo (where the oxygen may be replaced with sulfur or nitrogen)-5,5-dimethylimidazolidinyl- estradiol,cyproteron acetate, and the like. Specific taxoids comprising targeting moieties include 7-[imidazolidinyl-5", 5"-dimethyl-4"-oxo-3"-[(4"'-cyano-3"'-trifluoromethyl)phenyl]-2"-thioxo-1"ethylcarbamoxy]paclitaxel, (BP-196); 7-[3"-(carboxy) estradiol]paclitaxel, (BP-203); 2'-(2",3"-dihydroxypropylcarbonate)-7-(cyproterone acetate) paclitaxel, and the like.

Finally Z may be a hydrophilic polymer, particularly an addition polymer, comprising acidic groups as side chains, usually carboxy, or a poly(amino acid), e.g. monoclonal antibody. The polymer will have a weight average molecular weight of at least 5kD, usually at least 10kD, and not more than about 50okD, usually not more than about 300kD. Side chains will usually involve a heteroatom, such as nitrogen or oxygen, where nitrogen is present as amide or amino and oxygen is present as oxy or oxo, particularly non-oxo-carbonyl. The polymer may be a homopolymer or a copolymer, particularly a copolymer, having from 2 to 4, usually 2 to 3 different monomers. The polymer may be a random or block copolymer, preferably a random copolymer. Side chains may include carboxy, ethers, esters, carboxamides, cyano, where when a non-oxy-carbonyl is present, the functionality may be bonded to the backbone of the polymer by a carbon-carbon bond or a carbon-heteroatom bond. The monomers will generally be of from 3 to 8, usually 3 to 6 carbon atoms and have from 1 to 4 heteroatoms, particularly nitrogen and oxygen. Monomers of particular interest include vinyl ethers and esters, acrylic acid, esters and amides, and maleic anhydride, particularly copolymers comprising maleic anhydride in combination with one of the other monomers, particularly a non-acidic monomer. The other monomers will generally be of from 1 to 3, usually 1 to 2 heteroatoms. The ratio of monomers will generally be in the range of 1–10:1. With maleic anhydride, the maleic anhydride will usually be present in the ratio of about 1:1–10 to the other monomer. Usually fewer than about 50% of the monomers will be maleic anhydride.

In the subject polymer:paclitaxel conjugate taxoids, paclitaxel will be covalently attached to at least 1 monomer, usually at least about 10% of the monomeric units of the polymer. In general, paclitaxel will be attached to at least 1 in 10 of the monomer units of the polymer, usually to at least 1 in 8 of the monomeric units of the polymer, and will more usually be linked to at least 1 in 5 monomeric units of the polymer. The subject polymer:paclitaxel conjugate taxoids will comprise at least 30% paclitaxel (w/w), more usually at least 40% paclitaxel (w/w), and preferably at least 50% paclitaxel (w/w), usually not more than about 75%.

Of particular interest are paclitaxel:polymer conjugate taxoids where the paclitaxel moiety is attached to the polymer through a hydrolyzable linkage. For the most part the hydrolyzable linkages will be ester linkages, particularly where these linkages are in proximity to a carboxy group, usually on a β or γ carbon to the ester linkage, so as to provide for a taxoid with drug release half-life from the polymer of between 4 and 24 hours, and preferably between 5 and 7 hours. Specific polymer:paclitaxel conjugates of interest include methyl vinyl ether/maleic anhydride:paclitaxel conjugate, (BP-172), hydroxyethyl acrylate/acrylamide/maleic anhydride:paclitaxel conjugate, vinyl acetate/maleic anhydride:paclitaxel conjugate, vinyl acetate/acrylic acid:paclitaxel conjugate, and the like.

The subject taxoids may be synthesized in accordance with known synthetic procedures, where they may be prepared as crude mixtures comprising at least about 50 weight %, usually at least about 80 weight % of the total composition, preferably at least about 95%, more preferably at least about 99.5% up to absolute purity. The compositions comprising the subject taxoids may be purified using known procedures, e.g. crystallization or HPLC, to yield compositions where the subject taxoid is at least about 95 weight % of the composition.

The subject taxoids find use in the treatment of hosts suffering from a variety of different cellular proliferative diseases. Cellular proliferative diseases which may be treated with the subject taxoids include neoplasias, such as sarcomas, carcinomas, lymphomas, blastomas, melanomas, myelomas, Wilms tumor, leukemias, adenocarcinomas, and the like.

In treating a host suffering from a cellular proliferative disease, the subject taxoids may be formulated in a buffered medium providing an acidic pH, e.g. 2-4, preferably 3, and lyophilized for storage. The lyophilized composition may then be combined with a carrier or vehicle for convenient administration to the host. The subject taxoids may be formulated with any carrier or vehicle which provides for a physiologically acceptable composition. Preferred carriers or vehicles are those which are water miscible, e.g. aqueous, such as sterile water for injection, dextrose in saline, phosphate buffered saline, aqueous ethanol, propylene glycol, and the like. The concentration of the taxoid will vary, depending on its nature, i.e. activity, tolerance, etc., whether water soluble or targeted, the nature of the disease, the nature and frequency of administration, e.g. systemic or intralesional, and the like. Usually, the compound will be at a dosage level in the range of about one mg/kg to one g/kg, more usually in the range of about four to 500 mg/kg of host.

The subject compositions may be used in conjunction with other chemotherapeutic agents, such as antiandrogens, calcium channel blockers, immunostimulators, radiation stimulators, and individual chemotherapeutic agents, such as vinblastine, vincristine, cyclophosp amide, doxorubicin, cisplatin, and the like.

In addition to the carrier or vehicle component, other compounds, agents or excipients may be included in the subject compositions with beneficial result. Additional minor components are often included in the subject compositions for a variety of purposes. These components will for the most part protect the stability of the composition, control the pH, further reduce cytotoxic agent diffusion from the site of administration, etc. Illustrative components include buffers, viscosity enhancing agents, surface active agents, stabilizers, etc. These components are generally present in less than about 20 weight % of the total composition, usually less than about 10 weight %, more usually individually less than about 0.5 weight % and more than about 0.001% of the total composition. See Hoover, Dispensing of Medication (Mack Publishing, 1976). Of particular interest is the use of citric acid.

In treatments employing the subject taxoids, the physiologically acceptable compositions comprising the subject taxoids may be intravenously administered using any convenient means including syringe needle, catheter and the like.

Over an entire treatment procedure, where the taxoid compositions are employed by themselves or in conjunction with other therapies, the subject taxoid compositions may be administered once or a number of times, where the period between administrations may be on the order of hours, days or weeks. Thus, in a particular treatment procedure, a taxoid composition may be administered between 1 and 10 times, usually between 2 and 8 times, and more usually between 3 and 5 times. The total dosage administered to the patient over the entire course of treatment will depend on both the particular taxoid being employed, the host, e.g. human, being treated, the specific cellular proliferative disease, and the like, and may be determined empirically.

Effectiveness of a treatment employing the subject taxoids may be evaluated by a reduction in the rate of tumor growth, stabilization in the total volume of the tumor, a regression of the tumor, and the like.

The following examples are offered by way of illustration and not by way of limitation.

EXPERIMENTAL

Example 1. Synthesis of 2'-(2",3"-dihydroxypropyl carbonoxy)paclitaxel (Taxoid BP-171)

a. Taxoid BP-171 was synthesized by two alternative routes described below.

i. Synthesis of BP-171 through intermediate BP-165 2'-(alloc-paclitaxel).

BP-165 was prepared using a procedure of Carboni et al., J. Med. Chem. (1993) 36:513–515. To a solution of taxol (100 mg. 0.117 mmol) in $CH_2Cl_2$ (2.50 mL) was added allyl chloroformate (62.1 AL, 0.586 mmol) at $-70°$ C. with stirring. Maintaining $-70°$ C., 1.0 M $LiN[Si(CH_3)_3]_2$ in THF (100 mL, 0.100 mmol) was added to the reaction mixture. The reaction was removed from the cold bath and allowed to stir at room temperature for one hour. The reaction mixture was purified by preparative HPLC, without further workup, yielding 94.0 mg (85%) of 2'-(alloc)-taxol. Purity by HPLC was greater than 99%.

The resultant BP-165 was dissolved in t-BuOH (4.0 mL), which was added 10% formic acid (100mL), 70% t-BuOOH (23µL, 0.18 mmol), and then $OsO_4$ (1.15 mL of a 0.157 µL solution in t-BuOH, 0.18 mmol) with stirring at room temperature. Without further work-up, the product was purified by preparative HPLC, yielding 7.0 mg (87.5%) of BP-171. Purity by HPLC was greater than 98%.

The reaction scheme is provided in FIG. 1.

ii. Synthesis of BP-171 through intermediate BP-175 (2'-(solketalcarbonoxy)paclitaxel Paclitaxel (5.60 mg, $6.56 \times 10^{-3}$ mmol) was dissolved in anhydrous methylene chloride (560 µL). Triethylamine (5.48 µL, $39.36 \times 10^{-3}$ mmol, 6.0 equiv.) was added, followed by p-nitrophenylsolketalcarbonate (14.66 mg, 45.20 mmol, 7.50 equiv) and the mixture was stirred at room temperature under nitrogen. After 20 hours, the conversion was completed and the crude product was purified, without work-up, by preparative HPLC. A white solid was obtained (5.82 mg, $5.74 \times 10^{-3}$ mmol, 87% yield) in 98% HPLC purity. Treatment of the resultant BP-175 with aqueous formic acid yielded BP-171. The reaction scheme is shown in FIG. 1.

b. Synthesis of Taxoid Prodrugs Capable of in vivo Conversion to BP-171

Figure 2:
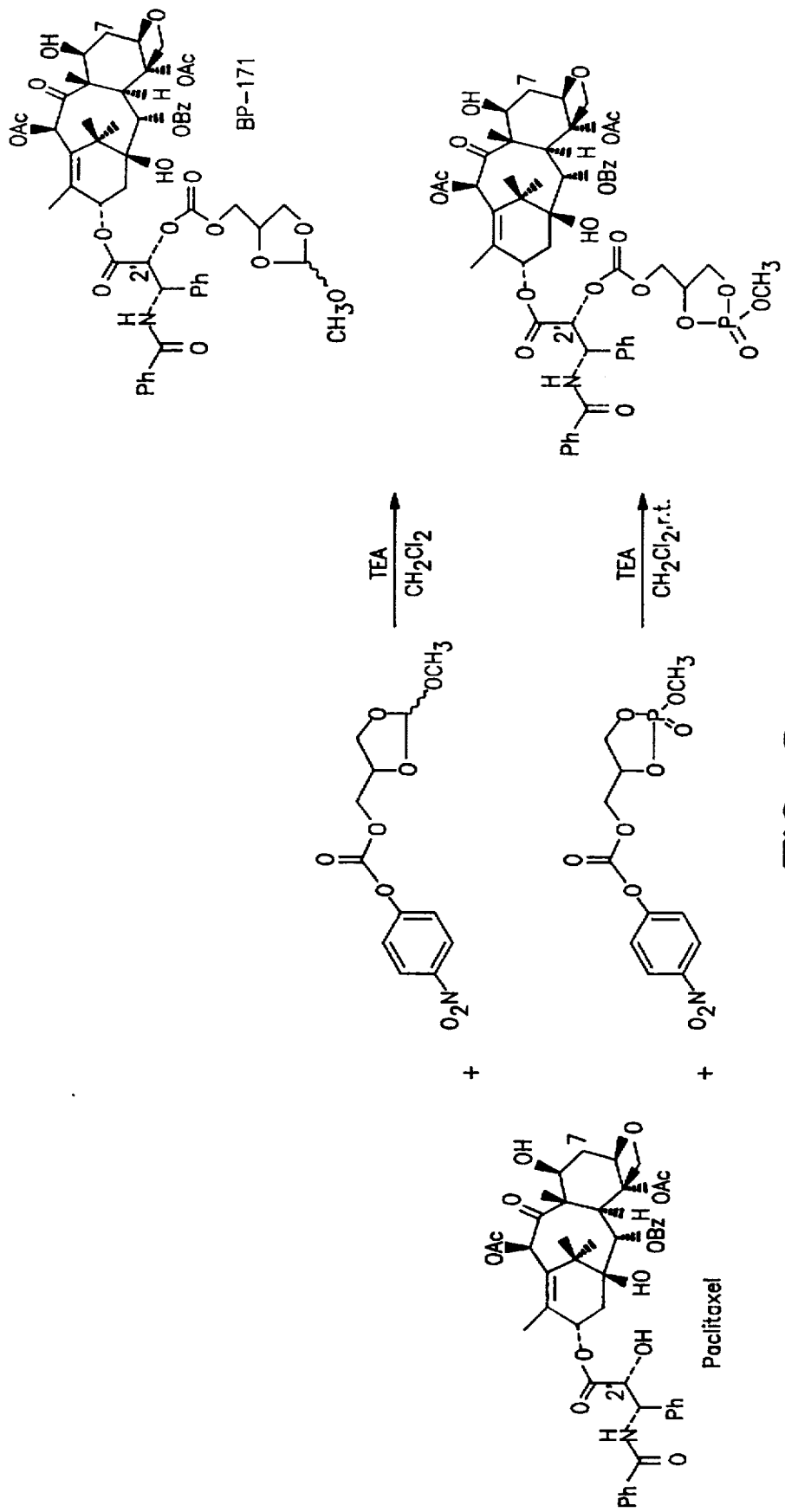
FIG. 2 provides the reaction scheme for the synthesis of two taxoids which may be converted in vivo to taxoid BP-171 shown in FIG. 1.

An alternate strategy for generating BP-171 is to protect the diol moiety with a potentially cleavable protecting group which may be cleaved by an enzymatic mechanism in vivo to yield BP-171.

i. Synthesis of 2'-[(methyl phosphate-1,3-dioxolane-4-methoxy)carbonoxy] paclitaxel Paclitaxel (2.95 mg, 0.0345 mmol) was dissolved in dry methylene chloride (300 Ml). Triethylamine (2.50 µl, 0.0207 mmol, 6.0 eq) was added, followed by p-nitrophenyl (methyl phosphate-1,3-dioxolane-4-methoxy) carbonate (8.05 mg, 24.15 mmol, 7.0 eq). The mixture was stirred at room temperature under nitrogen. The crude product was purified by preparative HPLC and afforded a clear solid. The reaction scheme is provided in FIG. 2.

ii. Synthesis of 2'-[O-(methoxy-1,3-dioxolane-4-methoxy) carbonoxy) paclitaxel

Paclitaxel (2.95 mg, 0.0345 mmol) was dissolved in dry methylene chloride (300 µl) Triethylamine (2.5 µl, 20.70 mmol, 6.0 eq) was added, followed by p-nitrophenyl (methoxy-1,3-dioxolane-4-methoxy) carbonate (7.75 mg, 0.0259 mmol, 7.5 eq). The mixture was stirred at room temperature overnight. Purification by preparative chromatography without any work-up afforded a white solid. The reaction scheme is provided in FIG. 2.

Example 2. Synthesis of 2'-(2",3"-dihydroxypropylcarbamoxy) paclitaxel (BP-174)

A round bottom flask charged with paclitaxel (10 mg, 0.01 mmol) solketalisocyanate (60 mg, 0.38 mmol) and a magnetic stir bar was placed under a $N_2$ atmosphere. THF (2 mL) was added to the mixture and the solution cooled to $-78°$ C. A solution of 1.0 M LiN[Si(CH$_3$)$_3$]$_2$ in THF (10 mL, 0.01 mmol) was added and the reaction solution stirred at $-78°$ C. for 30 minutes. At this time, a 0.1 M acetic acid solution in $H_2O$ (100 µL, 0.01 mmol) was added and the solution stirred at $-78°$ C. for 10 minutes. The solution was then allowed to reach room temperature and the volatiles removed under vacuum. 2'-(solketalcarbamoxy) paclitaxel (BP-173) was purified by preparative HPLC yielding 6.0 mg (51%). Purity by HPLC is greater than 99%.

A round bottom flask was charged with 2'-(solketalcarbamoxy) paclitaxel (2 mg, 0.002 mmol) (BP-173) and a magnetic stir bar. To this was added a solution of 50/50 formic acid MeOH (v/v) (200 µL) and the solution stirred 30 minutes at room temperature. At this time the volatiles were removed under vacuum. This analogous procedure was repeated twice on the remaining residue and 2'(2",3"-dihydroxypropyl-carbamoxy) paclitaxel (BP-174) purified by preparative HPLC yielding 1.8 mg (95%). Purity by HPLC 97%.

The presence of a hydrophilic functionality attached to the 2' moiety yields a taxoid which, like BP-171, exhibits enhanced water solubility as compared with paclitaxel.

Example 3. Additional Taxoids Comprising Hydrophilic Functionalities

Figure 3:
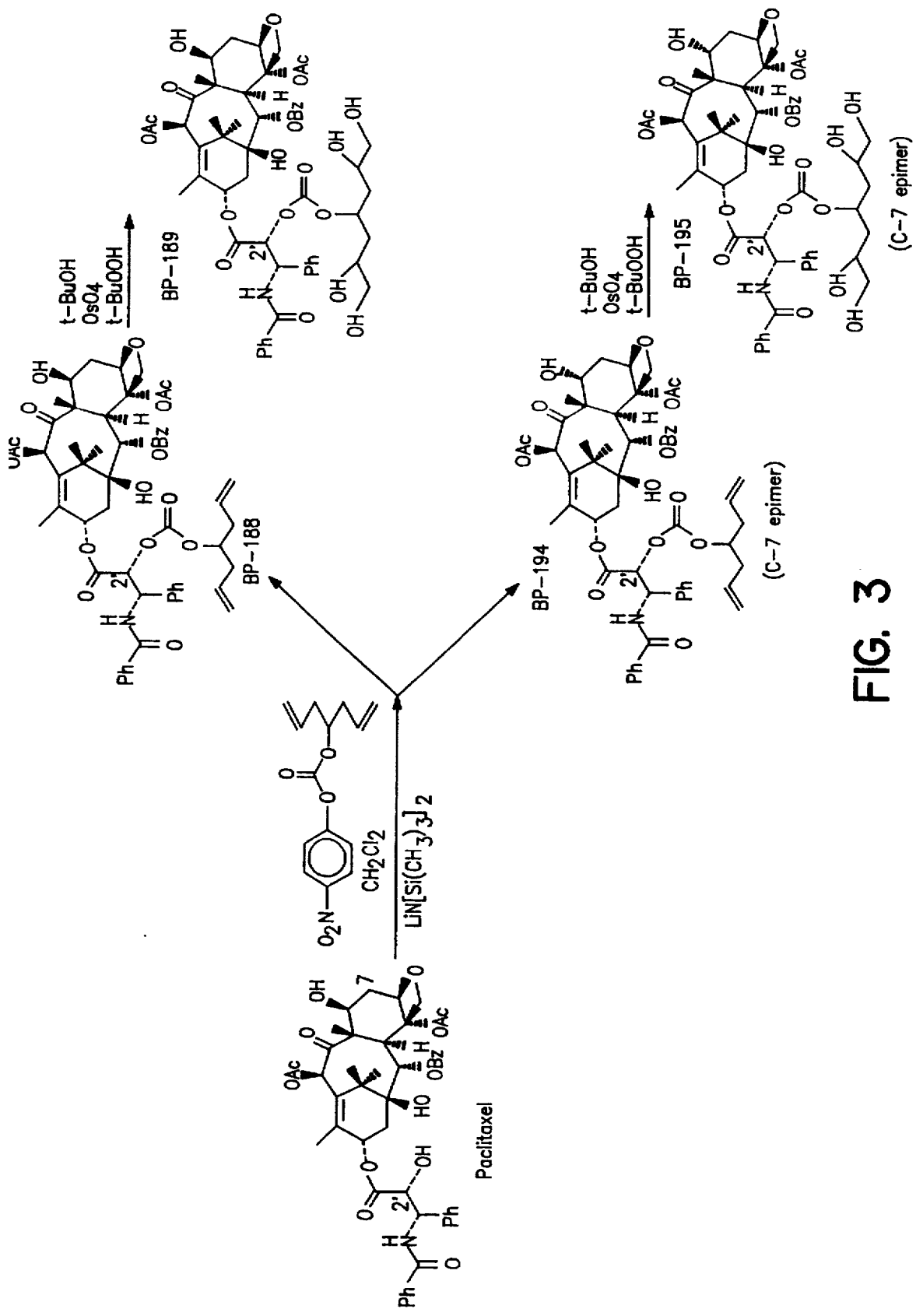
FIG. 3 provides the reaction scheme for the synthesis of taxoids BP-189 and BP-195, which taxoids comprise hydrophilic functionalities attached to paclitaxel at the C-2' position.
Figure 4:
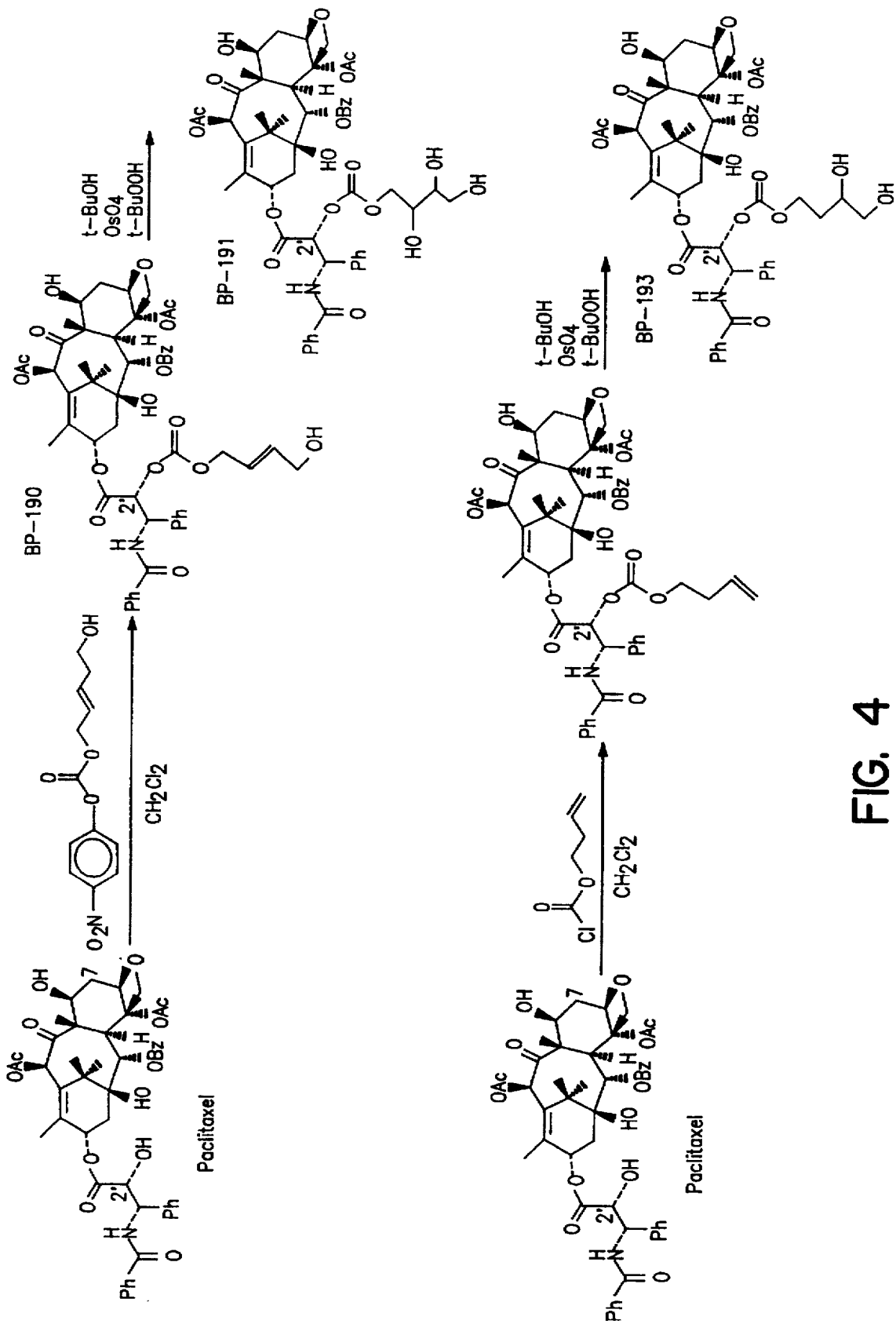
FIG. 4 provides the reaction scheme for the synthesis of taxoids BP-191 and BP-193, also comprising hydrophilic functionalities attached to paclitaxel at the C-2' position.
Figure 5:
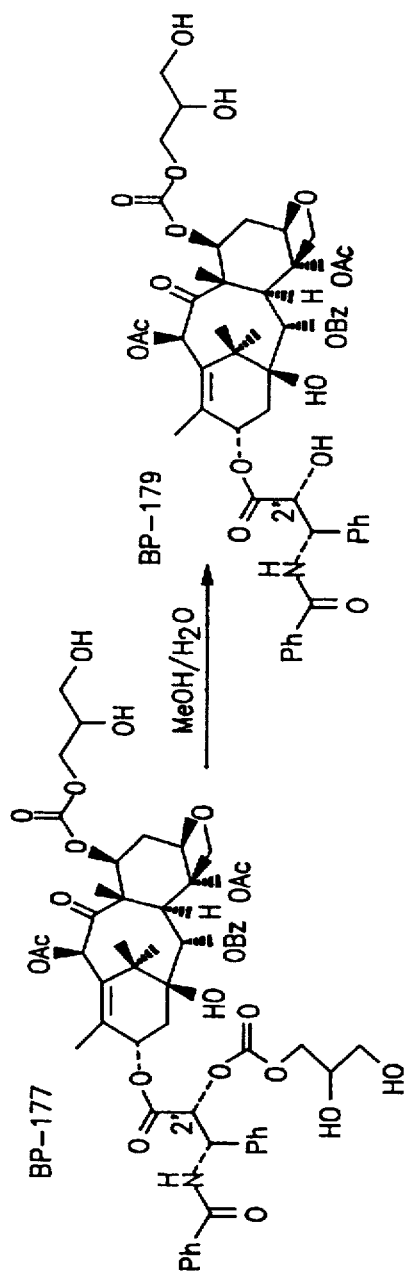
FIG. 5 provides the chemical structure of taxoid BP-177, a taxoid comprising a hydrophilic functional at both the C-2' and C7 positions, as well as the reaction scheme for the synthesis of BP-179 from BP-177.

Additional taxoids comprising hydrophilic functionalities were synthesized according to the scheme provided in FIGS. 3, 4 and 5. The structural variations between the different taxoids shown (BP-191, BP-193, BP-189, 195, BP-177 and BP-179)provide differences in solubility, plasma stability and pharmacokinetics as compared with paclitaxel.

Example 4. Synthesis of 2'-(triethylsiloxy), 7-(p-nitrophenylcarbonoxy) paclitaxel (BP-182)

BP-182, a useful intermediate in the synthesis of C7 substituted taxoids, was prepared as follows. A round bottom flask charged with paclitaxel (60 mg, 0.07 mmol) imidazole (90 mg, 1.32 mmol) and magnetic stir bar was placed under a $N_2$ atmosphere. $CH_2Cl_2$ (1.5 mL) was added and the solution was stirred at room temperature. To the solution was added portion-wise a solution of 1.0 M ClSiEt$_3$ in THF (5×100 µL, 0.5 mmol). The progress of the reaction was monitored by HPLC. Upon completion, the 2'-(triethylsiloxy) paclitaxel was purified by preparative HPLC yielding 51.3 mg (75%). Purity by HPLC 97%.

Figure 6:
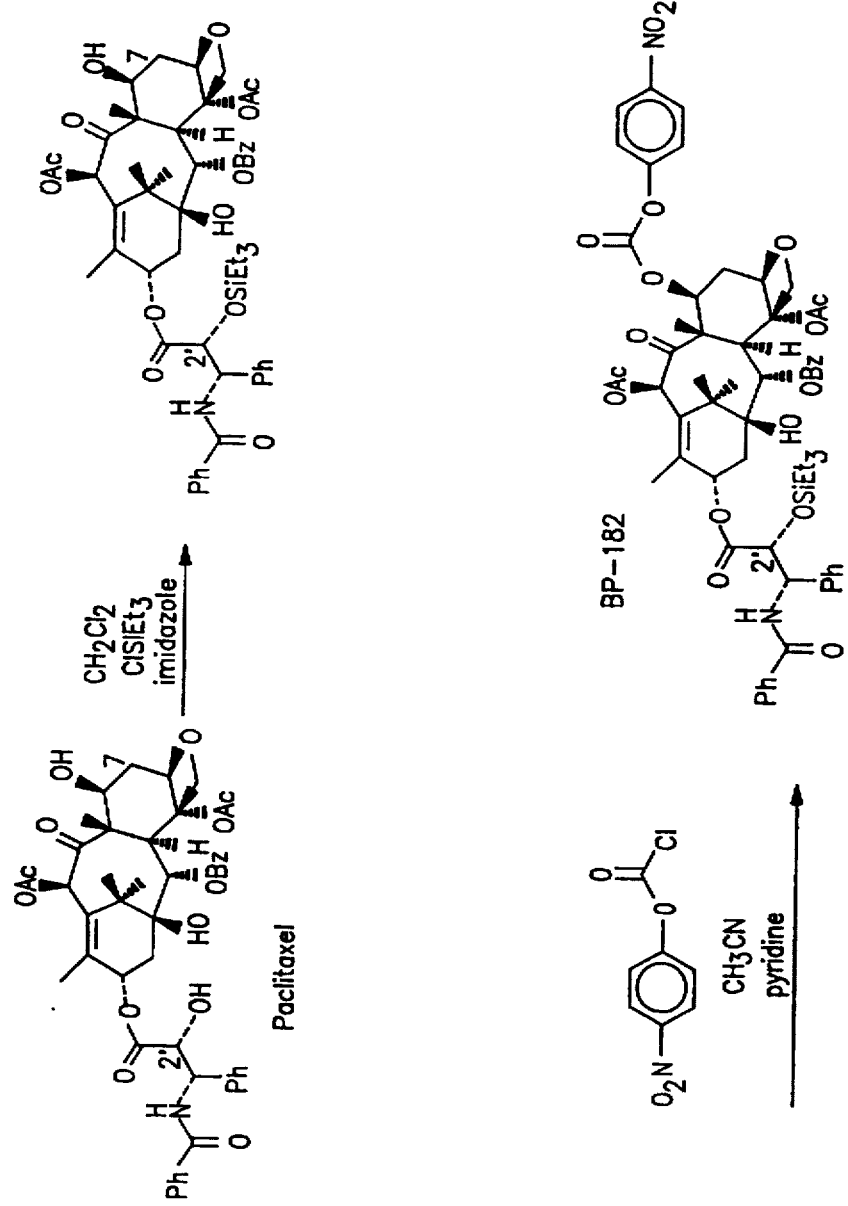
FIG. 6 provides the reaction scheme for the synthesis of BP-182, a useful intermediate in the synthesis of C7 substituted taxoids of the subject invention.

A round bottom flask charged wit 2'-(triethylsiloxy) paclitaxel (30 mg, 0.03 mmol), p-nitrophenylchloroformate (310 mg, 1.50 mmol) and a magnetic stir bar was placed under a $N_2$ atmosphere. A solution of pyridine (200 µL 0.247 mmol) in $CH_3CN$ (1.0 mL) was added and the mixture stirred at room temperature for 30 minutes. The product 2'-(triethylsiloxy), 7-(p-nitro-phenylcarbonoxy) paclitaxel (BP-182) was purified by preparative HPLC yielding 24.2 mg (69%). Purity by HPLC was 96%. The reaction scheme is provided in FIG. 6.

Example 5. Synthesis of Taxoids Comprising Targeting Moieties.

Taxoids comprising targeting moieties attached at the C7 position were prepared as follows.

a. Synthesis of 7-{imidazolidinyl-5", 5"-dimethyl-4"-oxo-3"-[4"'(cyano) 3'"(trifluoromethyl)phenyl]-2"-thioxo-1"-ethylcarbamoxy} paclitaxel (BP-196)

To a round bottom flask charged with 2'-(triethylsiloxy), 7-(p-nitrophenyl-carbonoxy) paclitaxel (BP-182) (28.0 mg, 0.014 mmol), 4[3-(2-aminoethyl-4-dimethyl-5-oxo-2-thioxo-1-imidazolidinyl]-2-(trifluoromethyl)-benzonitrile (2×8.0 mg, 0.44 mmol) and a magnetic stir bar was added $CH_2Cl_2$ (300 µL). The solution was stirred at room temperature for 4 hours and the product 2'-(triethylsiloxy)-7-[imidazolidinyl-5"-5"-dimethyl-4"-oxo-3"-[4"'(cyano),3"-(trifluoromethyl)phenyl]-2-thioxo-1'""ethylcarbamoxy] paclitaxel (BP-185) was purified by preparative HPLC yielding 8.2 mg (85%). Purity by HPLC 97%.

To a round bottom flask charged with the resultant BP-185 and a stir bar was added formic acid (250 mL). The solution was stirred at room temperature for 15 minutes and the volatiles removed under vacuum. 7-{imidazolianyl- 5"-5"-dimethyl-4"-oxo-5"-(-[4"'(cyano), 3"'-(trifluoromethyl)phenyl]-2-"thioxo-1'""ethylcarbamoxy} paclitaxel (BP-196) was purified by preparative HPLC yielding 4.6 mg (>99%). Purity by HPLC 99%. The reaction scheme is provided in FIG. 7. BP-196 is a tissue-specific, anti-androgen taxoid derivative.

b. Synthesis of 7-[3"-(carbonoxy)estradiol]paclitaxel (BP-203)

To a round bottom flask charged with 2'-(triethylsiloxy), 7-(p-nitrophenylcarbonoxy) paclitaxel (BP-182) (6.0 mg, 0.005 mmol), a-estradiol (6.0 mg, 0.022 mmol), DMPA (6.0 mg, 0.493 mmol) and a magnetic stir bar was added $CH_2Cl_2$ (300 µL). The solution was stirred at room temperature for 80 minutes and 2'-(triethylsiloxy)-7-[3"-(carbonoxy) estradiol] paclitaxel was purified by preparative HPLC yielding HPLC yielding 6.4 mg (96%). Purity by HPLC 99%. To a round bottom flask charged with the resultant 2'-(triethylsiloxy), 7-(3"-(carbonoxy)estradiol] paclitaxel (as prepared above) was added formic acid. The solution is stirred for 15 minutes and the volatiles removed under vacuum. 7-(3"-carbonoxy)estradiol] paclitaxel (BP-203) was purified by preparative HPLC. The reaction scheme is provided in FIG. 7.

c. Additional Taxoids Comprising Targeting Moieties.

Figure 7:
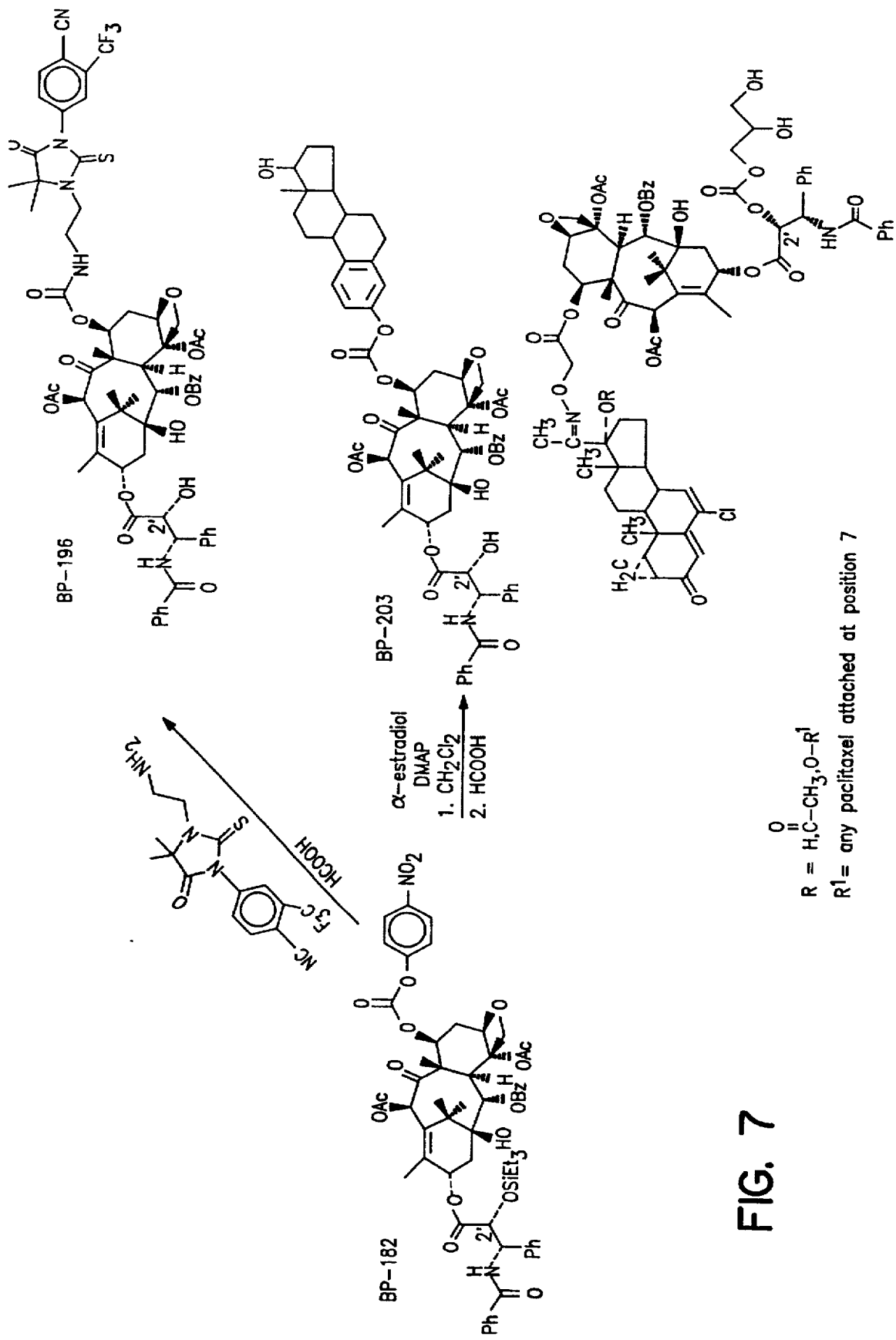
FIG. 7 provides the reaction scheme for the synthesis of taxoids 196 and 203 which comprise targeting moieties attached at the C7 position. Also shown is the chemical structure of a taxoid according to the subject invention having a targeting moiety (cyproterone acetate) attached to the C7 position and a hydrophilic functionality attached to the C-2' position.

An additional taxoid comprising a targeting moiety is the taxoid shown in FIG. 7, comprising cypropertone acetate coupled to BP-171 at the C7 position. The cypropertone acetate moiety provides for receptor homing activity while the hydrophilic moiety at the C-2' position of BP-171 provides for increased water solubility.

The above taxoids comprising targeting moieties may be useful in treating tumors possessing androgen/estrogen receptors.

Example 6. Synthesis of C-7 Substituted Taxoids Comprising Carbamate Linkers

Figure 8:
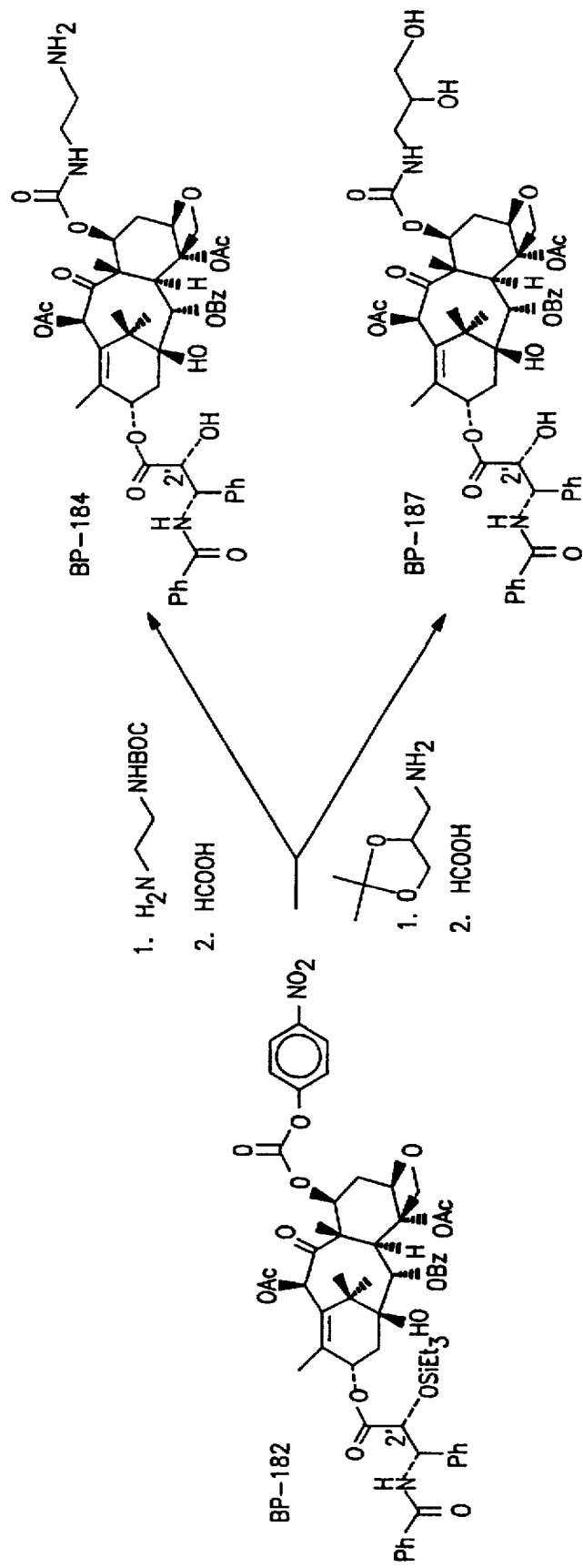
FIG. 8 provides the reaction scheme for taxoids having functionalities attached at the C7 position via linking groups potentially cleavable by carbamylases.

The intermediate BP-182 can be combined with hydrophilic amines to yield carbamate compounds. For example, BP-182 is combined with solketalamine to yield 2'-(triethylsiloxy)-7-(solketalcarbamoxy)paclitaxel intermediate which is then treated with acid to obtain 7-(2",3"-dihydroxypropylcarbamoxy)paclitaxel, as shown in the reaction scheme provided in FIG. 8.

Example 7. Synthesis of 2'-(D-6-galactopyranose carbonoxy) paclitaxel(BP-261)

A round bottomed flask charged with paclitaxel, p-nitrophenyl-(1,2:3,4-di-O-isopropylidene-D-galactopyranose carbonate) and a magnetic stir bar is placed under a $N_2$ atmosphere. To the flask is added a solution of triethylamine in $CH_2Cl_2$ and the solution stirred at room temperature. The product 2'-(1",2":3",4"-di-O-isopropylidene-D-galactopyranose carbonoxy) paclitaxel (BP-260) is purified by preparative HPLC.

A round bottom flask is charged with BP-260 and a magnetic stir bar. To this is added 50/50 formic acid and methanol (v/v) and the solution is stirred for 30 minutes at room temperature. The volatiles are removed in vacuo. The analogous procedure is repeated twice on the remaining residue and 2'-(D-6-galactopyranose carbonoxy) paclitaxel (BP-261) is purified by preparative HPLC.

Example 8. Synthesis of 2-[{2"-2''', 3'''-dihydroxypropyl)phenyl} carbonoxy] paclitaxel (BP-263)

Paclitaxel (4.2 mg, $4.52 \times 10^{-6}$ mol) was dissolved in anhydrous pyridine (420 AL). Dimethylaminopyridine (4.51 mg, 36.88×10 mol) was added to the solution followed by (o-allyl)phenyl-p-nitrophenyl carbonate (11.04 mg, $36.89 \times 10^{-6}$ mol). The mixture was stirred at room temperature overnight. Purification by preparative chromatography, without any work-up, afforded BP-262 (3.5 mg, $3.89 \times 10^{-6}$ mol, yield 80%).

Compound BP-262 (4.5 mg, $4.45 \times 10^{-6}$ mol) was dissolved in a 1:1 mixture of THF:t-butanol (900 µL). Formic acid was added (10% in $H_2O$, 100 µL) and the mixture was cooled to 0° C. t-Butyl peroxide (500 µL, 0.7% aqueous solution) and osmium tetroxide (500 µL, $10^{-5}$M solution in t-butanol) was added consecutively at 0° C. The clear solution was stirred at 0° C., then allowed to slowly warm to room temperature. Purification by preparative HPLC yielded BP-263.

Example 9. Synthesis of methyl vinyl ether/maleic anhydride:paclitaxel conjugate (BP-172)

Figure 9:
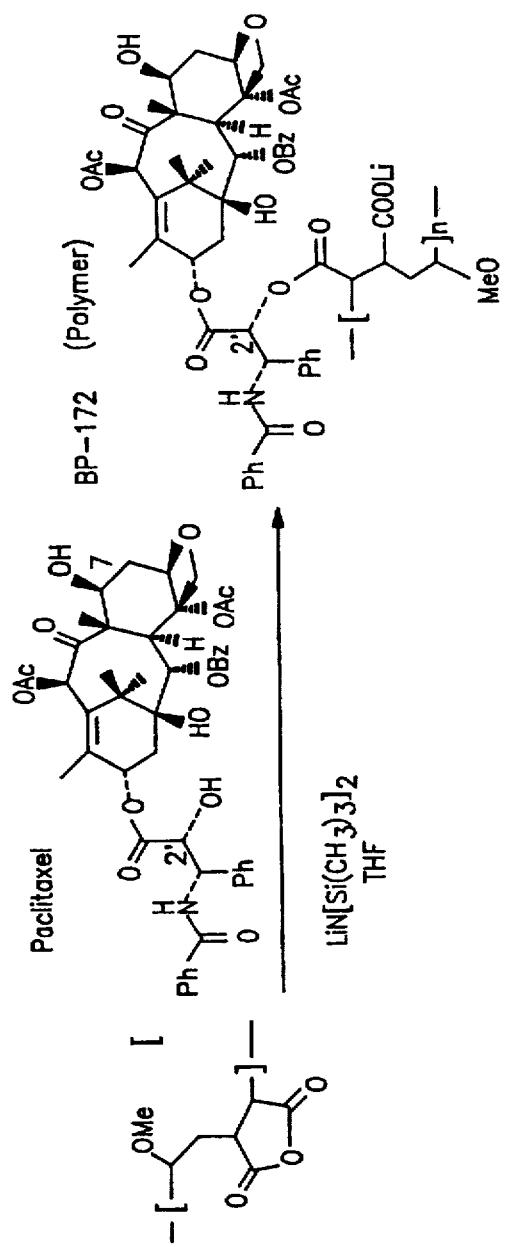
FIG. 9 provides the reaction scheme for the synthesis of the methyl vinyl ether/maleic anhydride:paclitaxel conjugate labeled BP-172.

Methyl vinyl ether/maleic anhydride copolymer (weight average molecular weight=50,000, 30 mg) was dissolved in dry THF (6mL) with heating. After the solution was cooled to room temperature, paclitaxel (60 mg, 0.07 mmol) was added, followed by $LiN[Si(CH_3)_3]_2$ (1 M solution in THF, 150 µL, 0.15 mmol) in a single portion. The reaction was allowed to proceed for 1 hour at which point HPLC (size exclusion chromatography) indicated that 70% of the paclitaxel added was bound to the polymer. The solvent was removed on a rotary evaporator and EtOAc (5 mL) was added. The precipitated solid was centrifuged, the supernatant decanted and the process repeated (3 mL EtOAc×4). After drying at 65° C. under high vacuum, the solid weighed 72 mg. Size exclusion chromatography showed that the polymer had a purity of 98%, with ca. 1% free paclitaxel present. U.V. analysis for paclitaxel content indicated 56% (w/w) which correlated with the HPLC-derived value. The reaction scheme is provided in FIG. 9.

The resultant polymer: drug conjugate (BP-172), containing up to 56% paclitaxel (w/w), is readily formulated in saline or 5% dextrose.

Example 10. Cytotoxic Activity of Selected Taxoids

Selected taxoids (BP-165, BP-171, BP-172, BP-173, BP-177, BP-178, BP-179, BP-182, BP-185, BP-188, BP-193, BP-194 and BP-196) were tested in a panel of human tumor cell lines to evaluate their cytotoxic activity as compared to paclitaxel. The results are provided in Table 1.

The results show that BP-171, BP-172, BP-179 and BP-193 exhibit cytotoxic activity equal to, or greater than, paclitaxel. Furthermore, taxoids BP-174, BP-177, and BP-196 each exhibit comparable cytotoxic activity to paclitaxel, i.e. their $IC_{50}$ value is within 1 or 2 orders of magnitude of the $IC_{50}$ value for paclitaxel. All of these taxoids are more water soluble than paclitaxel because they comprise hydrophilic functional groups and are readily formulated in standard aqueous vehicles.

TABLE 1

Cytotoxicity of Taxoids $IC_{50}$ (nM)

| Cell Line | | Taxol | BP-165 | BP-171 | BP-172 | BP-173 | BP-174 | BP-177 | BP-178 |
|---|---|---|---|---|---|---|---|---|---|
| Molt-4 | T-cell Leukemia | 3.08E–10 | 7.28E–09 | 3.39E–10 | 9.10E–10 | 2.09E–06 | 6.85E–07 | 7.03E–07 | 4.47E–07 |
| PC-3 | Prostate Carcinoma | 7.44E–09 | 8.46E–09 | 3.87E–10 | 1.54E–09 | 5.99E–06 | 1.10E–06 | 5.73E–08 | 1.35E–06 |
| DU-145 | Prostate Carcinoma | 2.12E–09 | 2.75E–08 | 4.29E–09 | 9.72E–09 | 2.24E–06 | 2.43E–06 | 91.4E–08 | 2.89E–06 |
| Ln-Cap | Prostate Carcinoma | 1.50E–09 | * | 6.19E–09 | 2.43E–08 | 1.00E–05 | * | 2.71E–08 | * |
| Ovcar-3 | Ovarian Carcinoma | 2.24e–09 | 6.47E–09 | 3.03E–10 | 1.75 09 | 5.24E–06 | 7.92E–06 | 5.00E–08 | 5.20E–07 |
| MCF-7 | Breast Carcinoma | 5.00E–09 | 9.70E–07 | 3.18E–09 | 1.00E–08 | * | 6.14E–07 | 3.35E–07 | 1.00E–08 |

| Cell Line | | BP-179 | BP-182 | BP-185 | BP-188 | BP-193 | BP-194 | BP-196 |
|---|---|---|---|---|---|---|---|---|
| Molt-4 | T-cell Leukemia | 1.99E–07 | 3.68E–08 | 1.00E–05 | 6.13E–07 | 3.97E–09 | 1.53E–06 | 1.47E–07 |
| PC-3 | Prostate Carcinoma | 3.24E–09 | 5.80E–08 | 1.35E–05 | 7.04E–08 | 1.55E–06 | 1.00E–06 | 3.22E–08 |
| DU-145 | Prostate Carcinoma | 2.05E–08 | * | * | 7.30E–07 | 1.40E–09 | 6.15E–05 | 8.67E–07 |
| Ln-CAP | Prostate Carcinoma | 2.05E–08 | 3.50E–08 | 1.00E–05 | 1.02E–07 | 1.95E–08 | 8.03E–06 | 1.31E–07 |
| Ovcar-3 | Ovarian Carcinoma | 5.00E–08 | 9.88E–08 | 5.90E–05 | 4.11E–07 | 5.50E–08 | 5.34E–07 | 500.E–08 |
| MCF-7 | Breast Carcinoma | 8.15E–07 | 1.00E–08 | * | 1.40E–07 | 8.65E–09 | 1.17E–06 | 9.89E–07 |

Example 11. In vivo efficacy of Taxoid BP-193

Figure 10:
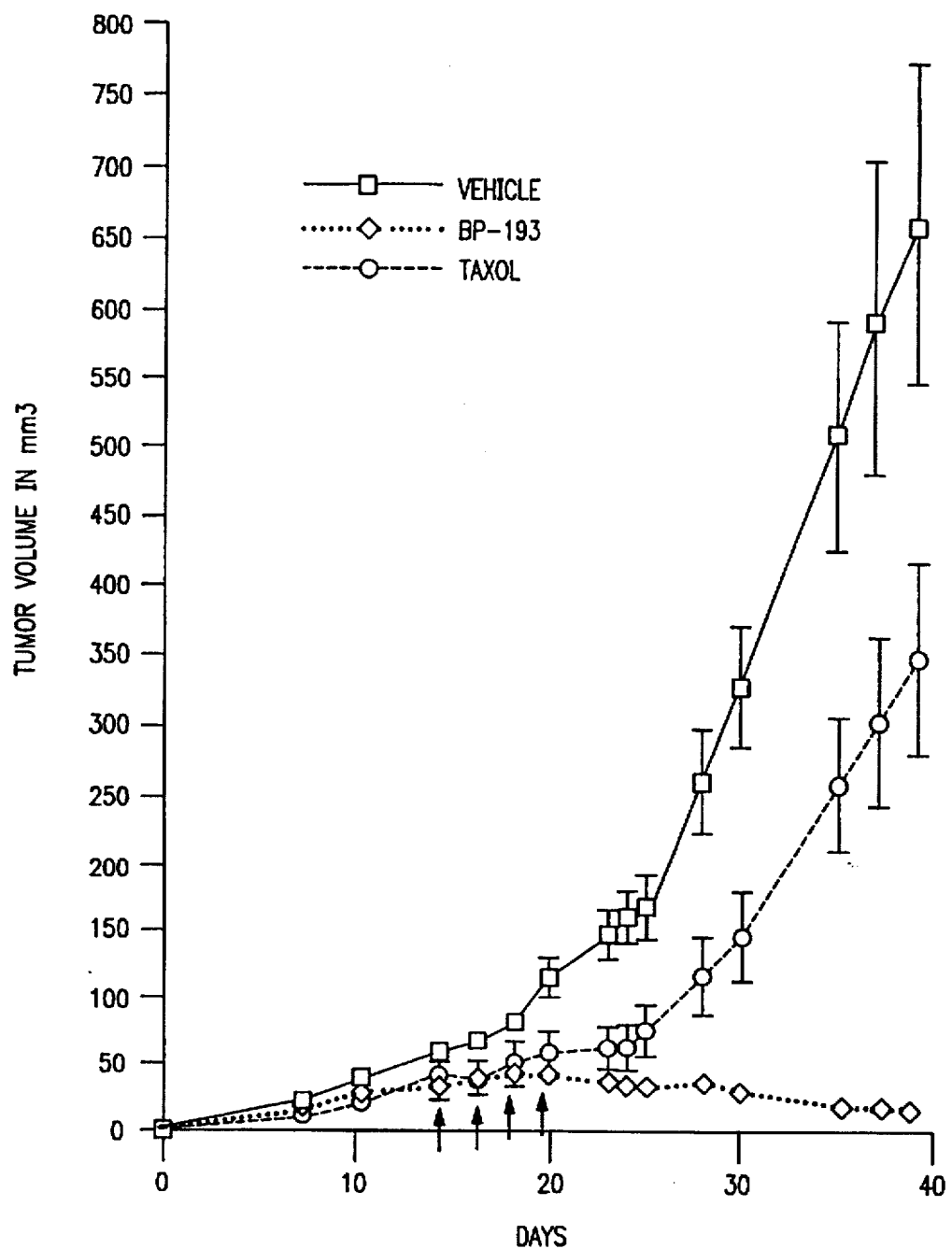
FIG. 10 provides a graph showing the growth of PC-3 tumors in athymic nude mice treated with the taxoids BP-193, Taxol® and a control.

The efficacy of Taxoid BP-193 as an anti-neoplastic agent was measured in vivo by studying its effects on the growth of an established PC-3 human prostate tumor as compared with a vehicle and Taxol® control. The results are provided in FIG. 10.

The results show that BP-193 exhibits significant anti-cellular proliferative activity, as measured by the reduction in tumor growth, while lacking the toxicity of paclitaxel. Furthermore, in all mice treated with BP-193, all tumors regressed to pretreatment levels.

It is evident from the above results and discussion that the novel taxoids provided have enhanced water solubility as compared with paclitaxel and/or improved pharmacological properties and substantially reduced mortality in animal models. Enhanced water solubility of the subject taxoids enables their formulation into a broader range of carriers or vehicles that are better tolerated by patients than formulations currently used for paclitaxel. Improved pharmacological properties found in the subject taxoids include decreased toxicity, improved plasma-stability and longer half-life, improved tissue distribution profiles and a variety of other factors leading to greater efficacy. In addition, paclitaxel derivatives provide for eenhanced cytotoxicity against prostate and other tumors, allowing for physiologically acceptable higher dosages in the treatment of cancers, so as to permit a broader dynamic range in the trreatment of neoplasia.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made hereto without departing from the spirit or scope of the appended claims.

What is claimed is:

1. A 2' and/or 7 paclitaxel substituted compound, or the 2' or 7 epimer thereof, wherein the substituent at the 2' and/or 7 position is:
   bonded to the oxygen at the 2' and/or 7 position of the paclitaxel group through an ether or ester bond; and is
   a hydrophilic group of from 3 to 12 carbon atoms and at least 1 heteroatom and up to 1 heteroatom per 1.25 carbon atoms, said hydrophilic group being substituted at the 7 position of the paclitaxel group only; or
   an organic molecule of less than 2.5 kD other than a poly(amino acid) binding specifically to a mammalian cellular receptor of cells susceptible to neoplasia.

2. A paclitaxel substituted compound according to claim 1, wherein said hydrophilic group is an aliphatic hydrophilic group of from 3 to 10 carbon atoms and chalcogen, nitrogen, phosphorus, and boron heteroatoms in-the range of 1.25 to 4 carbon atoms per heteroatom, there being at least one chalcogen or nitrogen atom.

3. A paclitaxel substituted compound according to claim 1, wherein said hydrophilic group comprises an aromatic hydrophilic group of from 3 to 1 2 carbon atoms and chalcogen, nitrogen, phosphorus, and boron heteroatoms in the range of 1.25 to 4 carbon atoms per heteroatom, there being at least one chalcogen or nitrogen atom.

4. A paclitaxel substituted compound according to claim 1, wherein said substituent is an organic molecule of less than 2.5 kD other than a poly(amino acid) binding specifically to a mammalian membrane receptor of breast, ovarian or prostate cells susceptible to neoplasia.

5. A 7 paclitaxel substituted compound, or the 7 epimer thereof, wherein the substituent at the 7 position is of the formula:

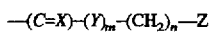

$$-(C=X)-(Y)_m-(CH_2)_n-Z$$

wherein:

X is selected from the group consisting of O, S and NH,
Y is selected from the group consisting of O, S, NH and $CH_2$;

n is an integer of from 0 to 6;

m is an integer of from 0 to 1, wherein m+n comes within the range of n, when Y is $CH_2$; and Z is: saturated aliphatic, alicyclic, aromatic, heterocyclic or combinations thereof, of from 2 to 10 carbon atoms having at least one heteroatom which is nitrogen or oxygen and up to 1 heteroatom per carbon atom, which heteroatoms are nitrogen, oxygen and phosphorous.

6. A 2' and/or 7 paclitaxel substituted compound, wherein the substituent at the 2' and/or 7 position is of the formula:

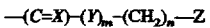

$$-(C=X)-(Y)_m-(CH_2)_n-Z$$

wherein:

X is selected from the group consisting of O, S and NH,
Y is selected from the group consisting of O, S, NH and $CH_2$;

n is an integer of from 0 to 6:

m is an integer of from 0 to 1, wherein m+n comes within the range of n, when Y is $CH_2$; and Z is a polyhydroxyalkyl group.

7. A 2' and/or 7 paclitaxel substituted compound, wherein the substituent at the 2' and/or 7 position is of the formula:

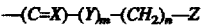

$$-(C=X)-(Y)_m-(CH_2)_n-Z$$

wherein:

X is selected from the group consisting of O, S and NH,
Y is selected from the group consisting of O, S, NH and $CH_2$;

n is an integer of from 0 to 6;

m is an integer of from 0 to 1, wherein m+n comes within the range of n, when Y is $CH_2$; and Z comprises a dioxolane group.

8. A 2' and/or 7 paclitaxel substituted compound, wherein the substituent at the 2' and/or 7 position is of the formula:

$$-(C=X)-(Y)_m-(CH_2)_n-Z$$

wherein:

X is selected from the grout consisting of O, S and NH,
Y is selected from the grout consisting of O, S, NH and $CH_2$.

n is an integer of from 0 to 6;

m is an integer of from 0 to 1, wherein m+n comes within the range of n, when Y is $CH_2$; and Z is a 2-phosphodioxolane group.

9. A 2' and/or 7 paclitaxel substituted compound, wherein the substituent at the 2' and/or 7 position is of the formula:

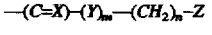

$$-(C=X)-(Y)_m-(CH_2)_n-Z$$

wherein:

X is selected from the group consisting of O, S and NH, Y is selected from the group consisting of O, S, NH and $CH_2$;

n is an integer of from 0 to 6;

m is an integer of from 0 to 1, wherein m+n comes within the range of n, when Y is $CH_2$, and Z is a polymeric subunit consisting of vinyl ether and maleic acid monomers, wherein said paclitaxel is bonded to a carboxy group of said maleic acid.

10. A 2' and/or 7 paclitaxel substituted compound, or the 2' or 7 epimer thereof, wherein the substituent at the 2' and/or 7 position is of the formula:

wherein:

X is selected from the group consisting of O, S and NH, Y is selected from the group consisting of O, S, NH and $CH_2$;

n is an integer of from 0 to 6;

m is an integer of from 0 to 1, wherein m+n comes within the range of n, when Y is $CH_2$; and Z is: a non-poly(amino acid) targeting moiety for a mammalian surface membrane receptor for mammary cells or an androgenic receptor, Z having a molecular weight in the range of 250D to 2.5D.

11. A paclitaxel substituted compound according to claim 10, wherein Z is a steroid.

12. A paclitaxel substituted compound according to claim 10, wherein Z comprises a 3-trifluoromethyl-4-cyanophenyl N-substituted imidazoline dione, and the nitrogen and sulfur analogs of said dione.

13. A method of reducing the number of neoplastic cells in a combination of cells, said method comprising:

adding to said combination of cells a cytotoxic amount of a compound according to claim 1.

14. A method of reducing the number of neoplastic cells in a combination of cells, said method comprising:

adding to said combination of cells a cytotoxic amount of a compound according to claim 5.

15. A method of reducing the number of neoplastic cells in a combination of cells, said method comprising:

adding to said combination of cells a cytotoxic amount of a compound according to claim 10.

16. A method for reducing the number of neoplastic cells in a mammalian host, said method comprising:

administering to said host a cytotoxic amount of a compound according to claim 1.

17. A method for reducing the number of neoplastic cells in a mammalian host, said method comprising:

administering to said host a cytotoxic amount of a compound according to claim 5 dispersed in an aqueous medium.

18. A method for reducing the number of neoplastic cells in a mammalian host, said method comprising:

administering to said host a cytotoxic amount of a compound according to claim 10.

19. A formulation comprising a physiologically acceptable liquid carrier and a compound according to claim 1.

20. A formulation comprising an aqueous physiologically acceptable liquid carrier and a compound according to claim 5.

21. 2'-(3",4"-dihydroxybutyl carbonoxy)paclitaxel.

22. 7-(2",3"-dihydroxypropyl carbonoxy)paclitaxel.

23. A substituted paclitaxel compound selected from the group consisting of (a) 2'-(2",3"-dihydroxypropyl carbonoxy) paclitaxel;

(b) 7-(3",4"-dihydroxybutyl carbonoxy) paclitaxel;

(c) 2'-(1",2",6",7"-tetrahydroxy-hept-4"-yl carbonoxy) paclitaxel;

(d) 7-(2",3"-dihydroxypropyl carbonoxy) paclitaxel;

(e) 2'-(2",3",4"-trihydroxybutyl carbonoxy) paclitaxel;

(f) 2',7-bis-(2",3"-dihydroxypropyl carbonoxy) paclitaxel;

(g) 7-(1",2",6",7"-tetrahydroxy hept-4"-yl carbonoxy) paclitaxel;

(h) 2'-(1",3",4"-trihydroxyisoureyl) paclitaxel;

(i) 7-(1",3"-diamino-2"-carboxy) paclitaxel;

(j) 2'-(2",4"-dihydroxythioureyl) paclitaxel;

(k) 2'-[(2-methylphospho-1,3-dioxolane-4-methoxy) carbonoxy] paclitaxel;

(l) 2'-[(5-methoxy-1,3-dioxolane-4-methoxy) carbonoxy] paclitaxel; and (m) 2'-(4"-trihydroxybutylaminobenzoyl) paclitaxel.

* * * * *